United States Patent [19]

Roland et al.

[11] 4,266,546
[45] May 12, 1981

[54] WRAPPED FOLDED TAMPONS

[75] Inventors: David R. Roland, Winneconne; Edward G. Wollangk, Oshkosh, both of Wis.

[73] Assignee: Kimberly-Clark Corporation, Neenah, Wis.

[21] Appl. No.: 124,620

[22] Filed: Feb. 25, 1980

[51] Int. Cl.³ .............................................. A61F 13/20
[52] U.S. Cl. ................................................... 128/285
[58] Field of Search ......................... 128/263, 270, 285

[56] References Cited

U.S. PATENT DOCUMENTS

| 3,322,123 | 5/1967 | Griswold et al. | 128/285 |
| 3,520,302 | 7/1970 | Jones | 128/285 |
| 3,762,413 | 10/1973 | Hanke | 128/285 |
| 3,845,767 | 11/1974 | Friese et al. | 128/285 |

FOREIGN PATENT DOCUMENTS 238593 7/1945 Switzerland ............................. 128/285

Primary Examiner—C. Fred Rosenbaum
Attorney, Agent, or Firm—Howard Olevsky; William D. Herrick

[57] ABSTRACT

A tampon which is designed to be folded, has foldable absorbent material, a fluid pervious outerwrap which is overlapped at its edge and a withdrawal string that encircles the tampon at the overlapped edge of the wrap. After folding, the string and overlapped edge are on the outside surface of the tampon.

9 Claims, 6 Drawing Figures

WRAPPED FOLDED TAMPONS

FIELD OF THE INVENTION

This invention relates to a tampon and particularly to a wrapped tampon.

BACKGROUND OF THE INVENTION

There are several considerations which are utilized in attempting to design a satisfactory tampon. Among these considerations are the prevention of leakage, ease of insertion and removal and ease of manufacturing.

Attempts to meet certain defined objectives amongst these considerations usually produce a lessening of efficacy in obtaining other objectives. For example, the prior art is replete with examples of insertion aids. These aids are usually in the nature of chemicals which provide some form of lubrication to minimize the friction upon insertion. Insertion aids, while performing this function, also form a barrier between the menstrual fluid and the absorbent material with a resultant interference in the efficiency of uptake.

Recently, absorbency characteristics of tampons have been improved by the inclusion of a class of compounds know as "superabsorbents". These materials rapidly absorb fluid and in so doing actually build up a negative pressure at the surface of the absorbent component of the tampons. As a result, when removal occurs extra force is needed to, in essence, tear the tampon away from the vaginal tissue which has been drawn tightly to the tampon surface.

Attempts have been made in the past to minimize this negative pressure by providing either physical or chemical barrier layers between the vaginal tissue and the superabsorbent material. For example, superabsorbent is used as a blend traditionally with more conventional absorbent material. In another approach, an outer wrap capable of retaining fluid has been used (see U.S. Pat. No. 4,056,103).

The tampon of this invention is one which is easily made and due to its unique and unusual construction is easy to insert and withdraw while offering a substantially complete barrier to leakage caused by bypass flow or heavy flow in a short period of time.

SUMMARY OF THE INVENTION

According to this invention a tampon having a fluid permeable outer wrap, an absorbent core and a withdrawal string is constructed so that the tampon is folded in half after wrapping. The withdrawal string is disposed about the outer surface of the tampon along the slightly overlapped edges of the wrap. As a result, the tampon during insertion has a wedge-shaped leading edge. After insertion is complete the tampon springs back because of the nature of the absorbent material putting pressure against the sides of the vaginal wall. During withdrawal, because the string encircles the outer surface of the tampon the downward facing edges are drawn together thereby minimizing the width of the tampon and providing for easier withdrawal due to this reduced width.

DETAILED DESCRIPTION OF THE INVENTION

Figure 1:
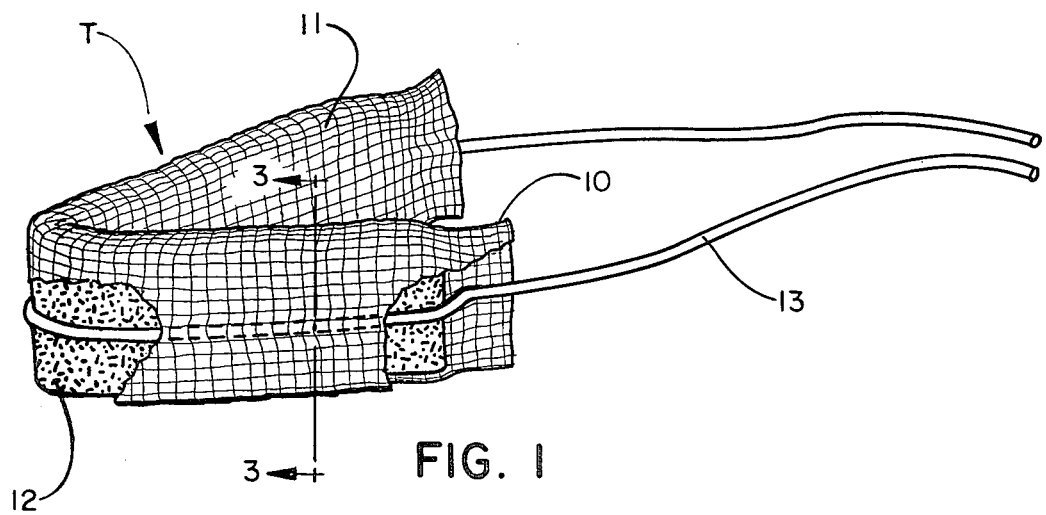

The subject invention can be readily understood by reference to the drawings in which FIG. 1 is a view partially in cross section of a bent tampon according to the subject invention.

Figure 2:
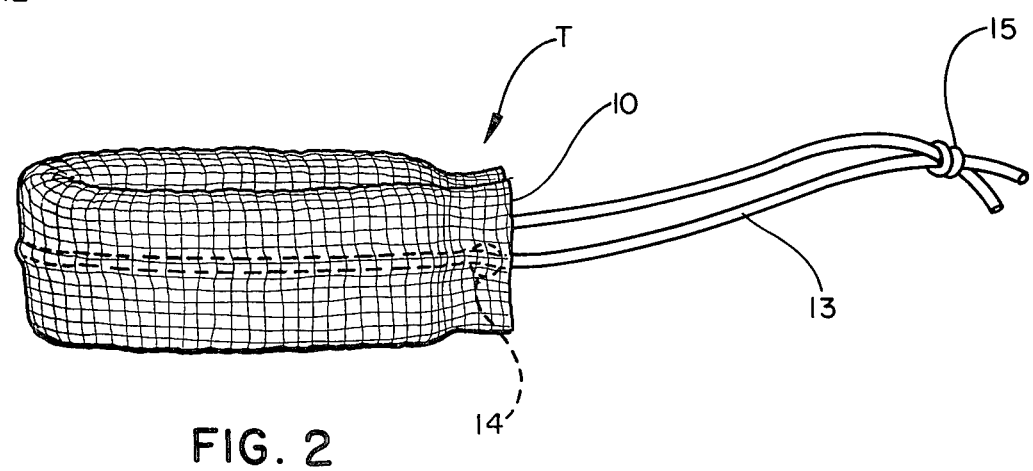

FIG. 2 is a view of a tampon completely folded and

Figure 3A:
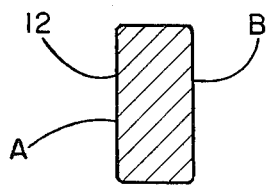

FIGS. 3A, B and C are cross sectional depictions of absorbent taken along line 3—3 of FIG. 1.

Figure 4:
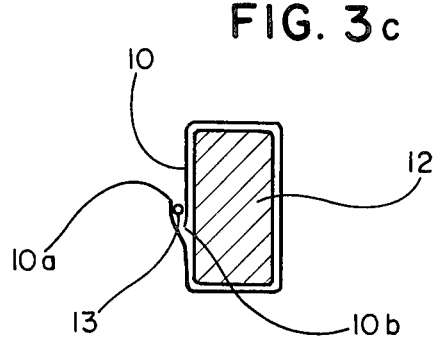

FIG. 4 is a representative cross sectional view of the wrapped tampon according to this invention.

Turning now to FIG. 1, a bent tampon partially in cross section is depicted therein. An outer wrap 10 surrounds an absorbent material 12 on the outer face of the tampon with an inner face of the outer wrap 11 present on the inward side after folding. As can be seen from the cross section on the outer side, a single thickness is used and in this particular embodiment the withdrawal string 13 is positioned between the wrap and the absorbent component.

The configuration depicted in FIG. 1 is that which is associated with the tampon in place with the sides of the tampon bowed slightly and pressing against the vaginal walls.

FIG. 2 depicts the tampon immediately prior to withdrawal where the sides of the tampon are abutting. This particular configuration has an adhesive area for attachment of the string at the portion of the wrapper 10 which extends beyond the absorbent layer 12. This adhesive area is represented by dotted lines 14.

FIG. 2 also indicates that the string may be knotted as depicted by 15 but this is not essential.

With regard to the fastening of the string, this may be done as indicated in FIG. 2 by conventional adhesive, by heat activatable adhesive either locally or along the path of the string or, if the string is made of a heat fusible material, it may be ultrasonically sealed or fused to the wrapper. If this is the case the configuration depicted at FIG. 4 is preferred. As can be seen in FIG. 4 the absorbent material 12 is surrounded by outer wrap 10 and the withdrawal string 13 is positioned between an upper and lower overlapping edge 10a and 10b of the wrapper. Fusing either by heat sealing or by ultrasonically sealing either locally or continuously or adhering by local application of heat to activate either periodic or continual application of heat activatable adhesive can be used to produce the wrapper seal and string attachment when the configuration depicted at FIG. 4 rather than that depicted in FIG. 1 is chosen. Because of this versatility, the positioning of the string 13 between the overlapped edges of the outer wrap 10a and 10b are currently preferred.

Figure 3B:
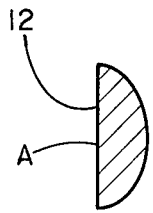
Figure 3C:
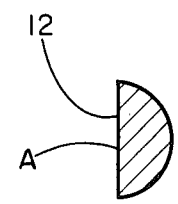

FIG. 3 depicts distinct cross sectional shapes of absorbent material for utilization in the tampon of this invention. The abutment surfaces A which provide the inner surface of the tampon after folding should be mating and preferably are flat so that the tampon can be folded to occupy the least amount of space upon withdrawal. The outer surface may be flat so that a rectangle is formed as is the case with FIG. 3A or may be arcuate as shown in FIGS. 3B and 3C. The configuration depicted in FIG. 3C is hemispherical so that when the tampon is folded a circular cross section is produced. In FIG. 3B an elliptical cross section is produced after the tampon is folded.

Currently, a rectangle with rounded edges such as that depicted at FIG. 3A is preferred due to ease of manufacture and assembly.

It is contemplated that a tampon according to this invention could contain superabsorbent as part of the absorbent component. The inclusion of the superabsorbent is well known but the characteristic ease of removal described in the specification would be particularly beneficial to overcome the difficulties inherent in removal where superabsorbent material is present as part of the absorbent core.

What is claimed is:

1. A tampon comprising a foldable absorbent material having a long axis and a short axis;
   a fluid pervious outer wrap disposed around the absorbent core with the long axis oriented edges of the wrap being overlapped and sealed;
   a withdrawal string attached to the outer wrap at the overlapped edges;
   the tampon being folded across the short side with the withdrawal string and the overlapping wrap disposed on the outer surface of the tampon.

2. The tampon according to claim 1 in which the string is positioned between the overlapped edges.

3. The tampon according to claim 1 wherein the string is adhesively attached.

4. The tampon according to claim 1 wherein the adhesive is heat activatable.

5. The tampon according to claim 1 wherein the withdrawal string and the wrap are heat fusible.

6. The tampon according to claim 1 wherein the wrap extends beyond the edge of the absorbent and the wrap and string are adhered in the extended portion.

7. The tampon according to claim 1 wherein the absorbent material is rectangular before folding.

8. The tampon according to claim 1 wherein the absorbent material is arcuate in cross section along one surface of the short axis.

9. The tampon according to claim 1 wherein the absorbent material contains superabsorbent.

* * * * *